United States Patent

Suga

(10) Patent No.: US 6,812,315 B2
(45) Date of Patent: Nov. 2, 2004

(54) OXAZOLIDINE COMPOUND AND CURABLE RESIN COMPOSITION

(75) Inventor: Kazuo Suga, Kanagawa (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 104 days.

(21) Appl. No.: 10/377,793

(22) Filed: Mar. 4, 2003

(65) Prior Publication Data

US 2003/0187176 A1 Oct. 2, 2003

(30) Foreign Application Priority Data

Mar. 15, 2002 (JP) ........................................ 2002-071835

(51) Int. Cl.$^7$ ................................................. C07F 7/10
(52) U.S. Cl. ........................ 528/27; 556/420; 556/445; 556/465; 556/482; 528/21; 528/28; 528/38; 528/73; 528/116; 528/121
(58) Field of Search .............................. 528/21, 27, 28, 528/73, 116, 121; 556/420, 445, 465, 482

(56) References Cited

U.S. PATENT DOCUMENTS

| 4,874,805 A | * | 10/1989 | Mulhaupt et al. | ........... 524/188 |
| 5,010,202 A | * | 4/1991 | Greco | ........................ 548/110 |
| 5,128,423 A | * | 7/1992 | Parrinello et al. | ........... 525/440 |

FOREIGN PATENT DOCUMENTS

| EP | 414962 A1 | * | 3/1991 | ............. C07F/7/04 |
| JP | 2001-192374 A1 | | 7/2001 | |
| JP | 2001-0041782 A1 | | 11/2001 | |

* cited by examiner

*Primary Examiner*—Margaret G. Moore
*Assistant Examiner*—Marc S Zimmer
(74) *Attorney, Agent, or Firm*—Rader, Fishman & Grauer PLLC

(57) ABSTRACT

Disclosed is an oxazolidine compound represented by the following formula (1).

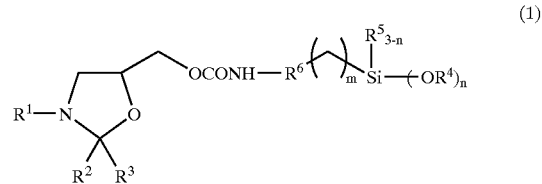

[$R^1$ represents a hydrocarbon group having 1 to 6 carbon atoms; $R^2$ and $R^3$ independently represent a hydrogen atom or a monovalent hydrocarbon group having 1 to 15 carbon atoms, or $R^2$ and $R^3$ combine to form an alicyclic ring or an aromatic ring; $R^4$ and $R^5$ independently represent a methyl group or an ethyl group; $R^6$ represents a single bond or —($R^7$—NHCOO—$R^8$—OCONH)$_p$—, $R^7$ and $R^8$ independently represent a divalent organic group, and p represents an integer of 1 to 15; m represents 2 or 3; n represents an integer of 1 to 3]. A curable resin composition using the oxazolidine compound as a latent curing agent have excellent curability and excellent storage stability, in particular, excellent storage stability in a state where the resin composition contains only the curable ingredient(s) and the latent curing agent.

2 Claims, No Drawings

OXAZOLIDINE COMPOUND AND CURABLE RESIN COMPOSITION

BACKGROUND OF THE INVENTION

1. Field of the Invention

The present invention relates to a novel oxazolidine compound that is used advantageously as a latent curing agent for curable ingredients such as epoxy resins, urethane resins and modified silicon sealant materials (i.e., terminal silyl group-containing resins) and to a curable resin composition containing such curable ingredients and such an oxazolidine compound.

2. Description of the Related Art

Heretofore, it has been known to use oxazolidine compounds as a latent curing agent for one-component curable resin compositions containing curable ingredients such as epoxy resins, urethane resins, and modified silicon sealant materials. This is to utilize the properties of oxazolidine compounds which is that they are readily hydrolyzed in the presence of humidity (moisture) to form secondary amines, which react with an epoxy group of epoxy resins or an isocyanate group of urethane prepolymers or they serve as a catalyst for condensation reaction of hydrolyzable silicon-containing group of hydrolyzable silicon-containing group-containing compounds to cause their curing.

However, oxazolidine compounds when used as a latent curing agent generally exhibit excellent depth curability of the obtained curable resin composition but have the problem that they have poor storage stability.

To cope with this problem, oxazolidine compounds having a bulky group in the vicinity of the nitrogen atom in the oxazolidine ring have been proposed in JP2001-192374 A (the term "JP XX-XXXXXX A" as used herein means an "unexamined published Japanese patent application"). In this publication, it is described that the oxazolidine compounds when used as a latent curing agent impart good storage stability and depth curability to the obtained curable resin composition.

SUMMARY OF THE INVENTION

However, the conventionally known oxazolidine compounds including those described in the above-mentioned publication when used as a latent curing agent have the problem that the obtained curable resin compositions have poor storage stability. In particular, they have the problem in that the storage stability is aggravated when the curable resin composition is in a state where it contains only a curable ingredient and a latent curing agent, that is, in a state where other compounding ingredients such as fillers, plasticizers and thixotropic agents are not compounded in it. If the storage stability of when the curable resin composition is in a state where it contains only a curable ingredient and a latent curing agent is low, it causes problems such as a reaction (increase of molecular weight) proceeds during its storage and when the resin composition is mixed with other compounding ingredients to produce a product, the viscosity of the product may increase to aggravate the workability or deteriorate the adhesion of the product to an adherend to decrease its performance such as adhesive properties.

Therefore, an object of the present invention is to provide a curable resin composition that has excellent curability and excellent storage stability, in particular, excellent storage stability in a state where it contains only a curable ingredient and a latent curing agent. Another object of the present invention is to provide a novel oxazolidine compound that is used as a latent curing agent in such a curable resin composition.

The present invention provides an oxazolidine compound (hereinafter, referred to as a "compound of the present invention") represented by the following formula (1).

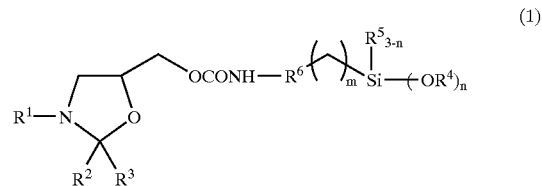

[$R^1$ represents a hydrocarbon group having 1 to 6 carbon atoms; $R^2$ and $R^3$ independently represent a hydrogen atom or a monovalent hydrocarbon group having 1 to 15 carbon atoms, or $R^2$ and $R^3$ combine to form an alicyclic ring or an aromatic ring; $R^4$ and $R^5$ independently represent a methyl group or an ethyl group; $R^6$ represents a single bond or —($R^7$—NHCOO—$R^8$—OCONH)$_p$—, $R^7$ and $R^8$ independently represent a divalent organic group, and p represents an integer of 1 to 15; m represents 2 or 3; n represents an integer of 1 to 3].

Also, the present invention provides a curable resin composition (hereinafter, referred to as a "composition of the present invention") containing (a) an epoxy group-containing compound, (b) an isocyanate group-containing compound, (c) a hydrolyzable silicon containing-group-containing compound, a mixture of (a) and (b) described above, or a mixture of (a) and (c) described above, and the above-mentioned oxazolidine compound.

The compound of the present invention when used as a latent curing agent for the curable ingredients such as epoxy resins, urethane resins, and modified silicon sealant materials have excellent curability, in particular excellent surface curability and excellent storage stability, in particular, excellent storage stability in a state where the resin composition contains only the curable ingredient(s) and latent curing agent, and thus can be used very effectively.

Also, since it contains the compound of the present invention, the curable resin composition of the present invention has excellent curability, in particular excellent surface curability and storage stability, in particular, excellent storage stability in a state where the resin composition contains only the curable ingredient(s) and latent curing agent, and thus can be used very effectively.

DETAILED DESCRIPTION

First, description will be made of the compound of the present invention.

The compound of the present invention is a compound represented by the following formula (1).

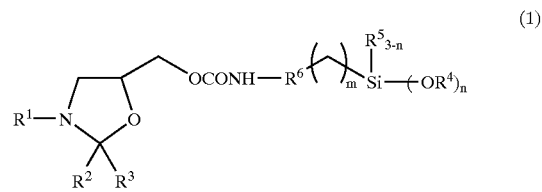

In the formula, $R^1$ represents a hydrocarbon group having 1 to 6 carbon atoms. Examples of $R^1$ include: a methyl group, an ethyl group, a propyl group, an isopropyl group, a butyl group, an isobutyl group, a s-butyl group, a t-butyl group, a pentyl group, an isopentyl group, a neopentyl group, a t-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group; and alkenyl groups or alkynyl groups that correspond to these alkyl groups.

Of those, $R^1$ is preferably a methyl group or an ethyl group since the obtained composition of the present invention has excellent surface curability. Also, it is particularly preferable if $R^1$ is a methyl group.

$R^2$ and $R^3$ independently represent a hydrogen atom or a monovalent hydrocarbon group having 1 to 15 carbon atoms, or $R^2$ and $R^3$ combine to form an alicyclic ring or an aromatic ring.

Examples of the monovalent hydrocarbon group having 1 to 15 carbon atoms include: a linear or branched alkyl group having 1 to 15 carbon atoms (for example, those alkyl groups having 1 to 6 carbon atoms exemplified for $R^1$), an alkenyl group or alkynyl group corresponding thereto, an aryl group that may be substituted with at least one substituent, an arylalkyl group, and a cycloalkyl group that may be substituted with at least one substituent. Specifically, they include: a linear alkyl group such as a methyl group, an ethyl group, a propyl group, a butyl group, a pentyl group, an octyl group, a dodecyl group, and a lauryl group; a branched alkyl group such as an isopropyl group, an isobutyl group, an s-butyl group, a t-butyl group, an isopentyl group, a neopentyl group, a t-pentyl group, a 1-methylbutyl group, and a 1-methylheptyl group; an alkenyl group such as a vinyl group, an allyl group, an isopropenyl group, and a 2-methylallyl group; an aryl group such as a tolyl group (o-, m-, p-), a dimethylphenyl group, and a mesityl group; an arylalkyl group such as a benzyl group, a phenethyl group, and a 60-methylbenzyl group; and a cycloalkyl group such as a cyclopentyl group and a cyclohexyl group.

Of those functional groups, the hydrocarbon group $R^2$ is preferably a bulky group such as a branched hydrocarbon group or a hydrocarbon group containing an alicyclic ring or an aromatic ring, for example, a branched alkyl group (e.g., an isobutyl group), an aryl group, an arylalkyl group, or a cycloalkyl group since a nitrogen atom in the oxazolidine ring is protected by steric hindrance of the substituent to weaken the basicity of the nitrogen atom to a great extent so that the obtained composition of the present invention has excellent storage stability.

In particular, of the above-mentioned functional groups, $R^2$ is preferably a hydrocarbon group of which the carbon at position 1 is a branching carbon or a ring-member carbon atom since the obtained composition of the present invention has particularly excellent storage stability.

Specific examples of the hydrocarbon group $R^2$ having a branching carbon at position 1 include an isopropyl group, an s-butyl group, a t-butyl group, a t-pentyl group, a 1-methylbutyl group, a 1-methylheptyl group, and an isopropenyl group.

Specific examples of the hydrocarbon group $R^2$ having a ring-member carbon at position 1 include aryl groups such as a phenyl group, a tolyl group (o-, m-, p-), and a dimethylphenyl group; arylalkyl groups such as an α-methylbenzyl group; and cycloalkyl groups such as a cyclopentyl group, a cyclohexyl group and a methylcyclohexyl group. The ring-member carbon atom may be either a carbon atom that constitutes an aromatic ring or an alicyclic ring.

Of those, $R^2$ is preferably an isopropyl group, a t-butyl group or a cyclohexyl group, in view of easy availability of raw materials and ease of synthesis.

Further, the aliphatic ring or aromatic ring formed by coupling $R^2$ with $R^3$ includes an aliphatic ring or aromatic ring having 4 to 10 carbon atoms. The aliphatic ring having 4 to 10 carbon atoms include, for example, a cyclobutyl group, a cyclopentyl group, a cyclohexyl group, a cycloheptyl group and a cyclooctyl group. The aromatic ring having 4 to 10 carbon atoms include, for example, a phenyl group, a benzyl group, a tolyl group (o-, m- ,p-) and a xylyl group.

$R^4$ and $R^5$ independently represent a methyl group or an ethyl group.

$R^6$ represents a single bond or $-(R^7-NHCOO-R^8-OCONH)_p-$. Here, $R^7$ and $R^8$ independently represent a divalent organic group, and p represents an integer of 1 to 15. $R^7$ is not particularly limited and includes, for example, residues that can be obtained by removing two isocyanate groups from the polyisocyanate compounds described hereinbelow. $R^8$ is not particularly limited and includes, for example, residues that can be obtained by removing two hydroxy groups from the polyol compounds described hereinbelow.

m represents 2 or 3.

n represents an integer of 1 to 3. n is preferably 2 or 3.

Preferred specific examples of the compound of the present invention include oxazolidine compounds represented by the following formulae (2) or (3).

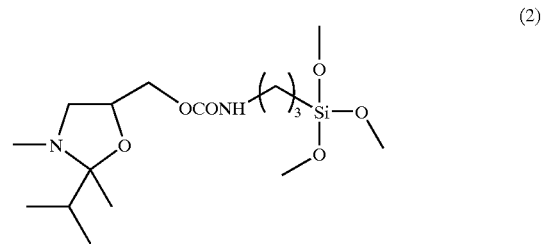

(2)

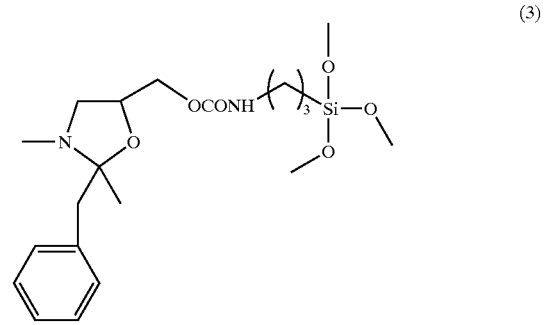

(3)

The method of producing the compound of the present invention is not particularly limited. For example, the compound of the present invention can be obtained by mixing an oxazolidine compound represented by the following formula (4) with an isocyanate silane compound represented by the following formula (5) and, if necessary, a reaction solvent such as ethyl acetate or butyl acetate and allowing reaction to occur at a temperature between room temperature and 80° C. for 4 to 24 hours. The symbols in the following formulae (4) and (5) have the same meanings as described above.

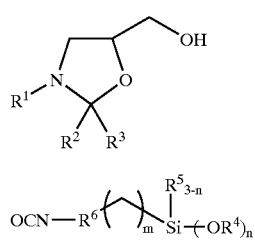

(4)

(5)

Here, the isocyanate silane compound represented by the above-mentioned formula (5) in which $R^6$ is —($R^7$—NHCOO—$R^8$—OCONH)$_p$—can be obtained by reacting the isocyanate silane compound represented by the above-mentioned formula (5) in which $R^6$ is a single bond, a polyisocyanate compound and a polyol compound. In that case, either a method in which the isocyanate silane compound represented by the above-mentioned formula (5) in which $R^6$ is a single bond, a polyisocyanate compound and a polyol compound are reacted simultaneously, or a method in which the isocyanate silane compound represented by the above-mentioned formula (5) in which $R^6$ is a single bond and a polyol compound are reacted and then a polyisocyanate compound is reacted with the resultant may be used.

The polyisocyanate compound used for the production of the isocyanate silane compound represented by the above-mentioned formula (5) in which $R^6$ is ($R^7$—NHCOO—$R^8$—OCONH)$_p$ is an isocyanate compound that has at least two isocyanate groups in its molecule and examples thereof include: 2,4-tolylene diisocyanate, 2,6-tolylene diisocyanate, 4,4'-diphenylmethane diisocyanate, 2,4'-diphenylmethane diisocyanate, p-phenylene diisocyanate, polymethylene polyphenylene polyisocyanate, 1,5-naphthalene diisocyanate, tolidine diisocyanate, triphenylmethane triisocyanate, bicycloheptane triisocyanate, tris(isocyanatephenyl)thiophosphate, and aromatic polyisocyanates such as a compound represented by the following formula (6) or hydrogenated compounds thereof;

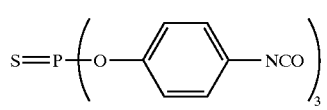

(6)

aliphatic polyisocyanates such as ethylene diisocyanate, propylene diisocyanate, tetramethylene diisocyanate, hexamethylene diisocyanate (HDI), tetramethylxylylene diisocyanate (TMXDI), trimethylhexamethylene diisocyanate, 1,6,11-undecane triisocyanate, and 1,3,6,hexamethylene triisocyanate; alicyclic polyisocyanate such as isophorone diisocyanate (IPDI); aryl aliphatic polyisocyanates such as xylylene diisocyanate, tetramethylxylene diisocyanate or hydrogenated compounds thereof; and isocyanurate forms, biuret forms, carbodiimide-modified polyisocyanate compounds and adducts with polyol compounds of these low molecular weight polyisocyanate compounds.

The isocyanurate form of the low molecular weight polyisocyanate compound includes, for example, isocyanurate forms such as IPDI and TMXDI, and an isocyanurate form obtained from TDI and HDI.

Preferred examples of adducts of the low molecular weight polyisocyanate compound and the polyol compound include adducts of trimethylolpropane (TMP) as the polyol compound. Specific examples thereof include TMXDI•TMP adduct represented by the following formula (7), which is derived from 1,1,1-trimethylolpropane (TMP) and TMXDI.

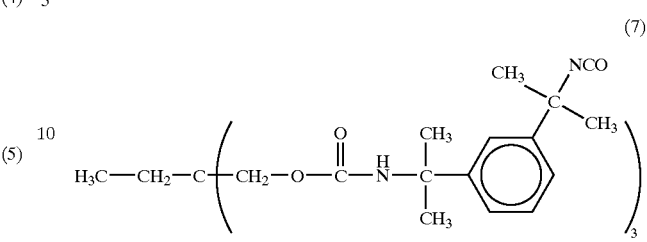

(7)

As the above-mentioned adduct, one commercially available under the trade name of CYTHANE 3160 (manufactured by Mitsui-Cytec, Ltd.) or the like may be used. The above-mentioned adduct may be a complete adduct in which all the hydroxy groups and isocyanate groups were completely reacted or may contain unreacted raw materials.

Also, as the polyisocyanate compound, urethane prepolymers obtained by reacting each of the above-mentioned isocyanate compounds with a polyol compound may be used. Examples of the polyol compound include polyether polyols, polyester polyols and other polyols as well as mixed polyols composed of these polyols.

Examples of the polyether polyol include: a product obtained by addition polymerization of at least one kind of alkylene oxide such as ethylene oxide, propylene oxide, butylene oxide, styrene oxide, and tetrahydrofuran with at least one compound having two or more active hydrogens.

Examples of the compound having two or more active hydrogens include polyalcohols, amines and alkanolamines.

Examples of the polyalcohols include: ethylene glycol, diethylene glycol, propylene glycol, dipropylene glycol, glycerin, 1,1,1-trimethylol propane, 1,2,5-hexanetolyol, 1,3-butanediol, 1,4-butanediol, 4,4'-dihydroxyphenylpropane, 4,4'-dihydroxyphenylmethane, and pentaerythritol. Examples of the amines include ethylene diamine, and propanolamine. Examples of the alkanolamines include ethanolamine, and propanolamine.

Specifically, the examples of the polyether polyol include polypropylene glycol, polyethylene glycol, and polypropylene triol. Also, it includes polytetramethylene glycol obtained by ring-opening polymerization of tetrahydrofuran.

Examples of the polyester polyol include: a condensation polymer of at least one kind of low molecular weight polyol such as ethylene glycol, propylene glycol, butanediol, pentanediol, hexanediol, cyclohexane dimethanol, glycerin, and 1,1,1-trimethylolpropane with at least one kind of low molecular weight carboxylic acid or oligomeric acid such as glutaric acid, adipic acid, pimelic acid, suberic acid, sebacic acid, terephthalic acid, isophthalic acid, and dimer acid; and a product obtained by ring-opening polymerization of propionlactone and valerolactone.

Examples of other polyols include low molecular weight polyols such as polycarbonate polyol, polybutadiene polyol, hydrogenated polybutadiene polyol, acrylic polyol; ethylene glycocol, diethylene glycol, propylene glycol, dipropylene glycol, butanediol, pentanediol, and hexanediol.

The mixing ratio of the polyol compound and the polyisocyanate compound when it is intended to obtain the urethane prepolymer as described above is such that the ratio of the number of the isocyanate groups of the polyisocyanate compound to the number of the hydroxy groups of the polyol compound (NCO/OH) is preferably 1.2 to 5, more preferably 1.5 to 3. Production of the urethane prepolymer can be performed in the same manner as the production of conventional urethane prepolymers, that is, by mixing both compounds in a predetermined ratio and heating them usually at 30 to 120° C., preferably 50 to 100° C. while stirring.

Among the above-mentioned polyisocyanate compounds, diisocyanates, which have two isocyanate groups in the molecule, or triisocyanates, which have three isocyanate groups in the molecule, are preferred.

Further, the polyisocyanate compound has a molecular weight of preferably 20,000 or less. When the molecular weight is 20,000 or less, the viscosity does not become too high, giving good workability.

These polyisocyanate compounds may be used singly or two or more of them may be used in combination.

As the polyol compound used in the production of the isocyanate silane compound represented by the above-mentioned formula (5) in which $R^6$ represents —($R^7$—NHCOO—$R^8$—OCONH)$_p$—, the polyol compounds used in the production of the above-mentioned polyisocyanate compounds may be used. Also, prepolymers having terminal OH groups obtained by reacting the polyisocyanate compound and the above-mentioned polyol compound in a mixing ratio, NCO/OH, of below 1 may be used.

The compound of the present invention undergoes ring opening of the oxazolidine ring due to hydrolysis to form a secondary amine in the presence of a large amount of moisture, which reacts with an epoxy group of an epoxy resin or an isocyanate group of a urethane prepolymer and causes curing. Also, it functions as a catalyst that catalyzes condensation reaction of a hydrolyzable silicon-containing group in a hydrolyzable silicon-containing group-containing compound and causes curing. At the same time, an alkoxysilyl group is hydrolyzed to cause a condensation reaction. Therefore, a resin composition containing the compound of the present invention as a latent curing agent exhibits an extremely high crosslinking density when cured, so that it has very excellent curability, in particular, very excellent surface curability.

On the other hand, in the presence of only a small amount of moisture, the compound of the present invention allows for the hydrolysis of alkoxysilyl groups to occur in preference to the ring opening of oxazolidine rings so that the latter is suppressed since the alkoxysilyl group has higher reactivity with water than the oxazolidine ring. In addition, the hydrolysis of alkoxysilyl groups to some extent gives only a little effect on the curing of the resin composition. Therefore, the resin composition containing the compound of the present invention as a latent curing agent has extremely excellent storage stability.

That is, the oxazolidine compounds described in JP 2001-192374 A referred to above involve a curing mechanism that is based only on the hydrolysis of the oxazolidine ring. In contrast, the compound of the present invention further causes curing based on the condensation reaction of alkoxysilyl groups, so that the resin composition containing the compound of the present invention has excellent curability.

Further, the oxazolidine compounds described in JP 2001-192374 A referred to above have a bulky group in the vicinity of the nitrogen atom in the oxazolidine ring and hence they suppress the reactivity with moisture. However, there is a room for the hydrolysis of the oxazolidine ring to occur, so that a resin composition containing such compounds has insufficient storage stability. On the contrary, in the case of the compounds of the present invention, the alkoxysilyl groups capture moisture so that substantially no hydrolysis of the oxazolidine ring occurs, and thereby the resin composition containing the compound of the present invention has excellent storage stability.

Furthermore, the compound of the present invention contains a urethane bond having strong polarity and produces an amino group and a silanol group at the time of curing, and hence when it is formulated into a composition for an adhesive, it has excellent adhesion to various kinds of metal, coatings, resins and glass. They have also excellent heat resistance.

In the case where the oxazolidine compounds are used as a latent curing agent for urethane resins, there occurs an addition reaction of secondary amines produced by the ring opening of the oxazolidine ring due to moisture in the air to the isocyanate groups of urethane prepolymers. On the other hand, polymerization reaction between the isocyanate groups of the urethane prepolymers also takes place to release carbonic acid gas. Such release of carbonic acid gas causes a problem since foaming may occur at the time of curing of the resin composition. In particular, when the oxazolidine compound contains an isocyanate group as a curable functional group, a reaction between the isocyanate group of the oxazolidine compound and the isocyanate group of the urethane prepolymer also takes place, so that considerable foaming occurs at the time of curing.

In contrast, in the case where the compound of the present invention is used, first, alkoxysilyl groups are hydrolyzed which causes a condensation reaction to take place due to moisture in the air to increase the crosslinking density. Subsequently, the above-mentioned reaction in which the secondary amines produced from the oxazolidine rings are added to the isocyanate groups of the urethane prepolymers takes place. These reactions take place in preference to the polymerization reaction between the isocyanate groups of the urethane prepolymers, so that the polymerization reaction between the isocyanate groups of the urethane prepolymers do not take place so often. Even when this reaction occurs, substantially no foaming as a result of gathering of carbonic acid gas occurs since the crosslinking density has already increased. Therefore, use of the compound of the present invention as a latent curing agent for urethane resins causes no problem of foaming.

Next, the composition of the present invention will be described.

The composition of the present invention contains (a) an epoxy group-containing compound, (b) an isocyanate group-containing compound, (c) a hydrolyzable silicon containing-group-containing compound, a mixture of (a) and (b) described above, or a mixture of (a) and (c) described above, and the above-mentioned compound of the present invention. Hereinafter, (a) the epoxy group-containing compound, (b) the isocyanate group-containing compound, and (c) the hydrolyzable silicon-containing group-containing compound used as curable ingredients in the composition of the present invention will be described.

(a) The epoxy group-containing compound is an uncured epoxy prepolymer having in average at least one epoxy group in the molecule and as such any conventionally known one may be used. Here, the average value of the epoxy group in the molecule is a value obtained by dividing the sum of the molecular weights of the epoxy group-containing compounds by the sum of epoxy equivalents.

Specifically, examples of the epoxy group-containing compound of which amines are the precursors include various isomers such as tetraglycidyldiaminodiphenylmethane, triglycidyl-p-aminophenol, triglycidyl-m-aminophenol, and triglycidylaminocresol.

In adittion to this, triglycidyl isocyanurate may also be mentioned.

Further, examples of the epoxy group-containing compound of which phenols are the precursors include bisphenol A type epoxy resins, hydrogenated bisphenol A type epoxy resins, brominated epoxy resins, bisphenol F type epoxy resins, bisphenol S type epoxy resins, phenol novolac type epoxy resins, cresol novolac type epoxy resins, resorcinol type epoxy resins, alicyclic epoxy resins, and modified epoxy resins.

Further, a polysulfide-modified epoxy resin having a main chain of a polysulfide skeleton represented by the following formula (8):

$$-(C_2H_4OCH_2OC_2H_4S_n)-\qquad(8)$$

(wherein n represents an integer of 1 to 5) is advantageously used. Specific examples of the polysulfide-modified epoxy resin include FLEP 50, FLEP 60, and FLEP 65 (trade names, manufactured by Toray Thiokol Company, Ltd.).

Among them, bisphenol A type epoxy resins are preferable in consideration that they are used as general-purpose epoxy resins.

Also, the epoxy group-containing compound is preferably a liquid that has a viscosity at 25° C. of 100,000 mPa·s or less. The composition of the present invention that contains such an epoxy group-containing compound has excellent rapid curability even at room temperature. Further, the epoxy group-containing compound having a viscosity at 25° C. of 100,000 mPa·s or less is, preferably one having an equivalent of 450 g/eq or less or a mixture of compounds combined so as to have an average equivalent of 450 g/eq or less. In particular, bisphenol A type epoxy resin, bisphenol F type epoxy resin, and the like, having an epoxy equivalent of 150 to 300 are preferable.

From the viewpoint of storage stability, aliphatic epoxy group-containing compounds such as hydrogenated bisphenol A type epoxy resins are preferable.

These epoxy group-containing compounds may be used singly or two or more of them may be used as mixtures.

(b) The isocyanate group-containing compound is an uncured urethane prepolymer having in average at least one isocyanate group in the molecule and as such any conventionally known one may be used. Here, the average value of the isocyanate group in the molecule is a value obtained by dividing the sum of the molecular weights of the isocyanate group-containing compounds by the sum of isocyanate equivalents.

Specifically, the above-mentioned isocyanate compounds having two or more isocyanate groups in the molecule may be mentioned. The isocyanate group-containing compounds may be used singly or two or more of them may be used as mixtures.

(c) The hydrolyzable silicon-containing group-containing compound is an uncured prepolymer having in average at least one hydrolyzable silicon-containing group in the molecule and as such any conventionally known so-called modified silicon sealant material may be used. Here, the average value of the hydrolyzable silicon-containing group in the molecule is a value obtained by dividing the sum of the molecular weights of the hydrolyzable silicon-containing group-containing compounds by the sum of the equivalents of the hydrolyzable silicon-containing groups.

The hydrolyzable silicon-containing group refers to a silicon-containing group that causes condensation reaction in the presence of moisture or a cross-linking agent when a catalyst or the like is optionally used. Examples of the hydrolyzable silicon-containing group include a halogenated silyl group, an alkoxysilyl group, an alkenyloxysilyl group, an acyloxysilyl group, an aminosilyl group, an aminooxysilyl group, an oxime silyl group, and an amide silyl group. Specifically, a halogenated silyl group, an alkoxysilyl group, an alkenyloxysilyl group, an acyloxysilyl group, an aminosilyl group, an aminooxysilyl group, an oxime silyl group, and an amide silyl group exemplified by the following formulae may be used appropriately.

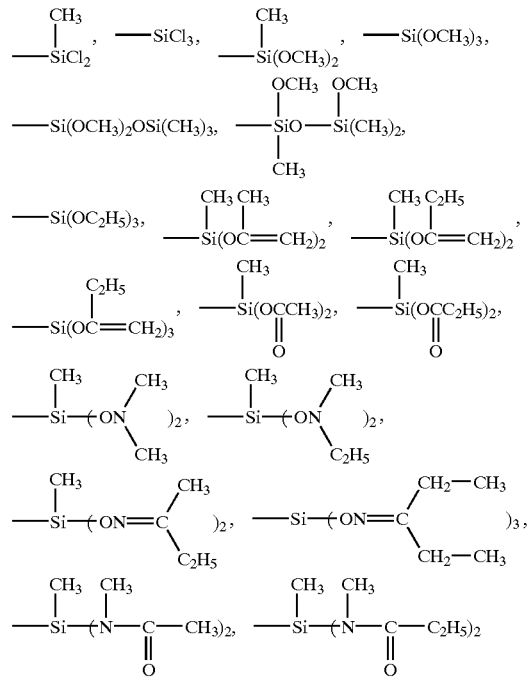

Of those, an alkoxysilyl group is preferable in respect of easy handling.

The alkoxy group that bonds to the silicon atom of the alkoxysilyl group is not particularly limited but preferably a methoxy group, an ethoxy group or a propoxy group may be mentioned in view of easy availability of raw materials.

The groups other than the alkoxy group that bond to the silicon atom of an alkoxysilyl group are not limited particularly but as those preferred, for example, a hydrogen atom or an alkyl group, an alkenyl group or an arylalkyl group, having 20 or less carbon atoms, such as a methyl group, an ethyl group, a propyl group, and an isopropyl group may be mentioned.

In the present invention, the hydrolyzable silicon-containing group may be present either on the terminals of the molecule or in the side chain, or in both.

Examples of the main chain of the hydrolyzable silicon-containing group-containing compound include polyethers such as alkylene oxide polymers, polyesters, ether/ester block copolymers, vinyl polymers, vinyl copolymers, diene polymers, and saturated hydrocarbons.

Examples of the polyether include those having repeating units represented by the following formulae.

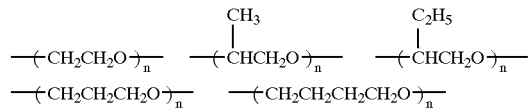

The polyether may be composed of only one kind of these repeating units or two or more of them.

Examples of the vinyl polymer, the vinyl copolymer, the diene polymer, and the saturated hydrocarbon include: polybutadiene, a styrene/butadiene copolymer, an acrylonitrile/butadiene copolymer, an ethylene/butadiene copolymer, an ethylene/propylene copolymer, an ethylene/vinyl acetate copolymer, an ethylene/acrylate copolymer, an ethylene/methacrylate copolymer, polyisoprene, a styrene/isoprene copolymer, an isobutylene/isoprene copolymer, polychloroprene, a styrene/chloroprene copolymer, an acrylonitrile/chloroprene copolymer, polyisobutylene, a polyacrylate, and a polymethacrylate.

The main chains of the hydrolyzable silicon-containing group-containing compound may be used singly or two or more of them may be used as mixtures.

As the hydrolyzable silicon-containing group-containing compound, bifunctional or polyfunctional alkoxysilanes, that is alkoxysilanes having two or more alkoxysilyl groups in the molecule are preferred. Those alkoxysilanes that have 3 to 20 alkoxysilyl groups are preferable in view of easy availability of raw materials.

The hydrolyzable silicon-containing group-containing compounds may be used singly or two or more of them. may be used as mixtures. When two or more of them are used as mixtures, it is preferred that a compound whose main chain is polyether and/or a compound whose main chain is a saturated hydrocarbon be contained in amounts of 10 wt % or more.

The molecular weight of the hydrolyzable silicon-containing group-containing compound is not particularly limited. However, a high-molecular one has high viscosity and its handling may in some cases become difficult, so that one having a number average molecular weight of 5,000 or less is preferable.

Such hydrolyzable silicon-containing group-containing compounds can be produced by a known method. Examples of commercially available products include MS polymer and EPION, manufactured by Kaneka Corporation and ExceStar manufactured by Asahi Glass Co., Ltd.

The composition of the present invention may contain a mixture of the above-mentioned ingredients (a) and (b), or a mixture of the above-mentioned ingredients (a) and (c), as curable ingredients. In these cases, the mixing ratio of the ingredients is not particularly limited and may be selected as appropriate depending on the purpose. Usually, it is in the range of preferably (a)/(b)=1/99 to 50/50 by weight or (a)/(c)=1/99 to 50/50 by weight.

Note that if the above-mentioned ingredients (b) and (c) are mixed with each other directly, the isocyanate group of the ingredient (b) and the alcohol or the like produced from the hydrolyzable silicon-containing group of the ingredient (c) react when curing with moisture occurs, thereby inhibiting the curing. Therefore, usually, these two cannot be used in combination. However, if the content of either one of them is of a very small quantity to such an extent that the object of the present invention is not harmed, they may be used in combination or the above-mentioned ingredient (a) may further be added.

In the composition of the present invention, the compound of the present invention may be used singly or two or more of them may be used as mixtures.

The content of the compound of the present invention in the composition of the present invention is preferably such that the molar ratio of the sum of the numbers of the epoxy group, isocyanate group and hydrolyzable silicon-containing group (hereinafter, referred to as "main functional groups") that the curable ingredients have to the number of the nitrogen atoms in the oxazolidine rings that the compound of the present invention has is in the range of 0.1 to 50, more preferably 0.5 to 20. If the molar ratio is within the above-mentioned range, the obtained composition of the present invention has extremely excellent curability and extremely excellent storage stability.

Because it contains the compound of the present invention, the composition of the present invention has excellent surface curability and excellent storage stability, in particular excellent storage stability in a state where the composition contains only the curable ingredient and the compound of the present invention serving as a latent curing agent and thus is useful.

As far as the object of the present invention is not harmed, the composition of the present invention may contain besides the compound of the present invention, other curing agent and/or latent curing agent that are typically used in an epoxy resin composition, a urethane resin composition, a modified silicon sealant material composition and so on.

For example, amine curing agents, acid or acid anhydride curing agents, basic active hydrogen compounds, imidazoles, polymercaptan curing agents, phenol resins, urea resins, melamine resins, isocyanate curing agents, latent curing agents, and ultraviolet curing agents may be mentioned.

In the case where the curable resin composition of the present invention contains these curing agents and/or latent curing agents, the compounding ratio of the sum of the curing agent ingredients including the compound of the present invention is such that the total active hydrogen content to the sum of the numbers of the main functional groups of the curable ingredients is preferably 0.1 to 5.0, more preferably 0.2 to 2.0, by equivalent ratio.

As far as the object of the present invention is not harmed, the composition of the present invention may contain various additives in addition to the above-mentioned various ingredients, as needed. Examples of such additives include fillers, plasticizers, silane coupling agents, thixotropic agents, pigments, dyes, age resistors, antioxidants, antistatic agents, flame retardants, tackifiers, dispersants, and solvents.

As the filler, those having various forms may be used, examples of which include: organic or inorganic fillers such as fumed silica, calcined silica, precipitated silica, ground silica, molten silica; diatomaceous earth; ferric oxide, zinc oxide, titanium oxide, barium oxide, magnesium oxide; calcium carbonate, magnesium carbonate, zinc carbonate; pyrophyllite clay, kaolin clay, calcined clay; and carbon black, as well as products thereof treated with fatty acids, resin acids, fatty acid esters or fatty acid ester urethane compounds.

Examples of the plasticizer include dioctyl phthalate (DOP), dibutyl phthalate (DBP); dioctyl adipate, isodecyl succinate; diethylene glycol dibenzoate, pentaerythritol ester; butyl oleate, methyl acetylricinoleate; tricresyl phosphate, trioctyl phosphate; and polyester of adipic acid and propylene glycol, polyester of adipic acid and butylene glycol.

Examples of the silane coupling agents that is suitable include trimethoxyvinylsilane, γ-glycidoxypropyltrimethoxysilane, isocyanate propyltrimethoxysilane, and ketiminated propyltrimethoxysilane in that they are general-purpose compounds.

Examples of the thixotropic agents include AEROSIL (a product of Nippon Aerosil Co., Ltd.), DISPARLON (a product of Kusumoto Chemicals, Ltd.), calcium carbonate, and Teflon (registered trademark).

Examples of the pigments include inorganic pigments such as titanium dioxide, zinc oxide, ultramarine blue, red iron oxide, lithophone, lead, cadmium, iron, cobalt, aluminum, hydrochlorides, and sulfates; and organic pigments such as azo pigments and copper phthalocyanine pigments.

Examples of the age resistors include hindered phenol-based compounds and hindered amine-based compounds.

Examples of the antioxidant include butylhydroxytoluene (BHT) and butylhydroxyanisole (BHA).

Examples of the antistatic agent include quaternary ammonium salts and hydrophilic compounds such as polyglycol and ethyleneoxide derivatives.

Examples of the flame-retardants include chloroalkyl phosphate, dimethyl/methyl phosphonate, bromine/phosphorus compound, ammonium polyphosphate, neopentylbromide polyether and brominated polyether.

Examples of the tackifier include terpene resin, phenol resin, terpene/phenol resin, rosin resin, and xylene resin.

The above-mentioned additives may be used accordingly in combination.

The method of producing the composition of the present invention from the ingredients as described above is not particularly limited. Preferably, a method is used in which the above-mentioned ingredients are sufficiently kneaded under reduced pressure or in an atmosphere of an inert gas such as nitrogen in a stirring apparatus such as a mixer to make a uniform dispersion.

The composition of the present invention is used advantageously as an adhesive, a sealant, a coating composition, an anti-corrosive coating composition, a primer, a coating material, a foaming material, or the like, for civil construction, concrete, wood, metals and the like.

EXAMPLES

Hereinafter, the present invention will be described specifically by examples. However, the present invention should not be considered to be limited thereto.

Examples 1 to 4 and Comparative Examples 1 and 2

Ingredients shown in Table 1 below were compounded in the formulation (part by weight) as shown in Table 1 to obtain resin compositions. The obtained resin compositions were evaluated of surface curing time (surface curability) and change in viscosity (storage stability) as follows.

<Surface Curing Time (Surface Curability)>

Each resin composition was charged in a polypropylene-made cup-shaped vessel of 1 cm in height as closely as possible to its upper limit, and the vessel was left to stand in an environment of a temperature of 20° C. and a relative humidity of 60%. During the standing, the surface of the resin composition was touched with a polyethylene sheet and the time in which the resin composition no longer adhered to the sheet was measured.

The results obtained are shown in Table 1.

<Change in Viscosity (Storage Stability)>

The viscosity of each resin composition immediately after it was prepared was measured and then the resin composition was charged in an airtight vessel under seal. After this was stored at 70° C. for one day (24 hours), the viscosity of the resin composition was measured. The viscosity after the storage was divided by the viscosity immediately after it was prepared to calculate a change in viscosity. The viscosity was measured at 20° C. by use of E type viscometer with a 3° cone.

The results obtained are shown in Table 1.

TABLE 1

|  | Example | | | | | Comparative Example | |
| --- | --- | --- | --- | --- | --- | --- | --- |
|  | 1 | 2 | 3 | 4 | 5 | 1 | 2 |
| Epoxy group-containing compound | 100 | 70 | 70 | 70 | 15 | 70 | 70 |
| Isocyanate group-containing compound |  | 30 |  | 30 |  | 30 | 30 |
| Hydrolyzable silicon-containing group-containing compound |  |  | 30 |  |  |  |  |
| Oxazolidine compound 1 | 30 | 30 | 20 |  |  |  |  |
| Oxazolidine compound 2 |  |  |  | 30 |  |  |  |
| Oxazolidine compound 3 |  |  |  |  |  | 15 |  |
| Oxazolidine compound 4 |  |  |  |  |  |  | 20 |
| Oxazolidine compound 5 |  |  |  |  | 85 |  |  |
| Surface curing time (h) | 18 | 10 | 12 | 14 | 12 | 50 | 30 (foaming occurred) |
| Change in viscosity (fold) | 1.2 | 1.1 | 1.1 | 1.1 | 1.1 | 3.0 | 5.0 |

The ingredients shown in Table 1 described above are as follows.

(1) Epoxy group-containing compound: Bisphenol A type epoxy resin, EP4100E (trade name, manufactured by Asahi Denka Co., Ltd.)

(2) Isocyanate group-containing compound: urethane prepolymer synthesized from a mixture of tri-functional PPG (polypropylene glycol) having a number average molecular weight of 5,000 and TMXDI in a ratio of NCO/OH=2

(3) Hydrolyzable silicon-containing group-containing compound: Modified silicon sealant material, MS Polymer (trade name, manufactured by Kaneka Corporation)

(4) Oxazolidine compound 1: Oxazolidine compound represented by the above-mentioned formula (2)

(5) Oxazolidine compound 2: Oxazolidine compound represented by the above-mentioned formula (3)

(6) Oxazolidine compound 3: Oxazolidine compound represented by the following formula (9)

(7) Oxazolidine compound 4: Oxazolidine compound represented by the following formula (10)

(8) Oxazolidine compound 5: Oxazolidine compound represented by the following formula (11) (molecular weight 1,400)

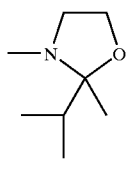

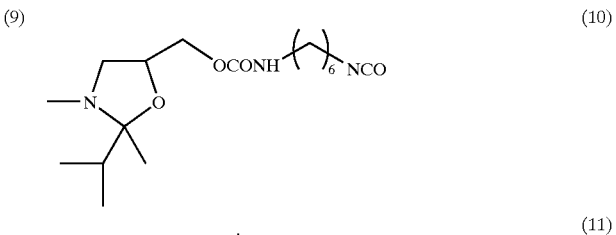

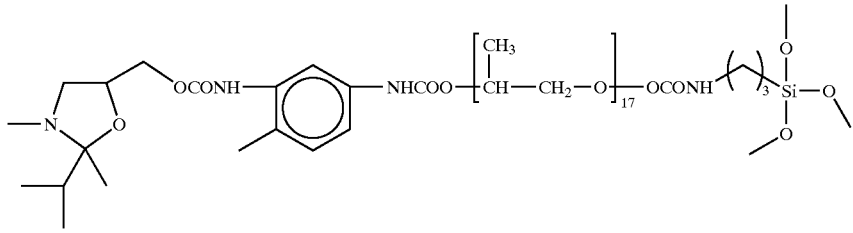

As will be apparent from Table 1, the curable resin compositions of the present invention containing the compound of the present invention (Examples 1 to 5) had excellent surface curability and did not form foams at the time of curing. Also, they had small changes in viscosity in a state where they contained only the curable ingredient(s) and latent curing agent, that is, they had excellent storage stability.

In contrast, in the case where the conventional oxazolidine compound having no alkoxysilyl group was used as a latent curing agent (Comparative Example 1), the resin composition had poor surface curability as well as poor storage stability. Also, in the case where the oxazolidine compound having an isocyanate group was used as a latent curing agent (Comparative Example 2), the surface curability of the resin composition was improved as compared with Comparative Example 1 but was still poorer than those in the Examples and in addition the resin composition formed foams at the time of curing. Further, the resin composition had a storage stability that was poorer than Comparative Example 1.

This application claims priority on Japanese patent application No. 2002-71835, the contents of which are hereby incorporated by reference.

What is claimed is:

1. An oxazolidine compound represented by the following formula (1).

[$R^1$ represents a hydrocarbon group having 1 to 6 carbon atoms; $R^2$ and $R^3$ independently represent a hydrogen atom or a monovalent hydrocarbon group having 1 to 15 carbon atoms, or $R^2$ and $R^3$ combine to form an alicyclic ring or an aromatic ring; $R^4$ and $R^5$ independently represent a methyl group or an ethyl group; $R^6$ represents a single bond or —($R^7$—NHCOO—$R^8$—OCONH)$_p$—, $R^7$ and $R^8$ independently represent a divalent organic group, and p represents an integer of 1 to 15; m represents 2 or 3; n represents an integer of 1 to 3].

2. A curable resin composition containing (a) an epoxy group-containing compound, (b) an isocyanate group-containing compound, (c) a hydrolyzable silicon containing-group-containing compound, a mixture of (a) and (b) described above, or a mixture of (a) and (c) described above, and the oxazolidine compound according to claim 1.

* * * * *